United States Patent
Goto et al.

(10) Patent No.: US 8,043,491 B2
(45) Date of Patent: Oct. 25, 2011

(54) PARTICLE-DISPERSED COMPLEX AND SOLID ELECTROLYTIC SENSOR USING IT

(75) Inventors: Takashi Goto, Miyagi (JP); Teiichi Kimura, Miyagi (JP); Hajime Suzuki, Tochigi (JP); Keiichiro Jinushi, Tokyo (JP)

(73) Assignee: Furuya Metal Co., Ltd., Tokyo (JP)

( * ) Notice: Subject to any disclaimer, the term of this patent is extended or adjusted under 35 U.S.C. 154(b) by 857 days.

(21) Appl. No.: 10/590,079

(22) PCT Filed: Sep. 16, 2004

(86) PCT No.: PCT/JP2004/013561
§ 371 (c)(1),
(2), (4) Date: Aug. 21, 2006

(87) PCT Pub. No.: WO2005/080955
PCT Pub. Date: Sep. 1, 2005

(65) Prior Publication Data
US 2007/0170399 A1    Jul. 26, 2007

(30) Foreign Application Priority Data
Feb. 20, 2004  (JP) .................. 2004-045325

(51) Int. Cl.
*G01N 27/407* (2006.01)
(52) U.S. Cl. ................... 204/424; 427/249.1
(58) Field of Classification Search .......... 204/424
See application file for complete search history.

(56) References Cited

U.S. PATENT DOCUMENTS

| | | | |
|---|---|---|---|
| 5,372,849 A * | 12/1994 | McCormick et al. | 427/253 |
| 5,543,239 A * | 8/1996 | Virkar et al. | 429/33 |
| 5,814,719 A * | 9/1998 | Suzuki et al. | 73/23.31 |
| 6,471,745 B1 * | 10/2002 | Foley et al. | 95/54 |
| 7,097,875 B2 * | 8/2006 | Clyde et al. | 427/115 |
| 2002/0108872 A1 * | 8/2002 | Symons et al. | 205/784 |
| 2003/0026921 A1 * | 2/2003 | Ueno et al. | 427/595 |
| 2003/0088116 A1 * | 5/2003 | Kawano et al. | 556/136 |

(Continued)

FOREIGN PATENT DOCUMENTS
JP          63-319050         12/1988
(Continued)

OTHER PUBLICATIONS

Smith et al., "Evaluation of Precursors for Chemical Vapor Deposition of Ruthenium" Thin Solid Films 376, pp. 73-81 (2000).*

(Continued)

*Primary Examiner* — Harry D Wilkins, III
*Assistant Examiner* — Bryan D. Ripa
(74) *Attorney, Agent, or Firm* — Oblon, Spivak, McClelland, Maier & Neustadt, L.L.P.

(57) ABSTRACT

A particle-dispersed complex which can serve as a very active electrochemical catalyst used as the sensor electrode of a solid electrolyte sensor such as an oxygen sensor and an exhaust gas sensor that are sensitive even at low temperature, or as the electrode or the like of an electrochemical device or the like such as an electrolysis or a battery or the like by dispersing without aggregating ruthenium system fine particles having a very small particle size into a carbon matrix phase to keep ruthenium system fine particles in a high catalyst active state. The particle-dispersed complex is characterized by comprising fine particles that have a particles size of 5-100 nm, contain ruthenium element as a constituent element, and are dispersed in a matrix mainly containing carbon, and by having conductivity.

12 Claims, 12 Drawing Sheets

U.S. PATENT DOCUMENTS

| | | | |
|---|---|---|---|
| 2003/0230484 A1* | 12/2003 | Jain et al. | 204/424 |
| 2004/0018416 A1 | 1/2004 | Choi et al. | |
| 2004/0129202 A1* | 7/2004 | Gruen et al. | 117/68 |

FOREIGN PATENT DOCUMENTS

| | | |
|---|---|---|
| JP | 2001-250563 | 9/2001 |
| JP | 2002-88494 | 3/2002 |
| JP | 2003-187851 | 7/2003 |
| JP | 2003-282077 | 10/2003 |
| JP | 2003-317728 | 11/2003 |
| JP | 2004-103549 | 4/2004 |
| KR | 1999-007223 | 1/1999 |

OTHER PUBLICATIONS

Goto et al., "Electrochemical Properties of Iridium-Carbon Nano Composite Films Prepared by MOCVD" Scripta Materialia 44, pp. 1187-1190 (2001).*

Kimura et al., "Preparation of RuO2-YSZ Nano-Composite Films by MOCVD" Surface and Coatings Technology 167, pp. 240-244 (2003).*

Lian et al., "Ru-Doped Nanostructured Carbon Films" Diamond and Related Materials 11, pp. 1890-1896 (2002).*

"The Element Carbon" accessed from http://education.jlab.org/itselemental/ele006.html on Sep. 15, 2010.*

Definition of "Carbon Black" as accessed from http://dictionary.reference.com on Apr. 7, 2011.*

"Preparation of Iridium Films by MOCVD and Their Application for Oxygen Gas Sensors" by Goto et al., Inorganic Materials 33(10) pp. 1017-1021 (1997).*

"Effect of Oxygen Gas Addition on Preparation of Iridium and Platinum Films by Metal-Organic Chemical Vapor Deposition" by Goto et al., Materials Transactions, JIM 40(3) pp. 209-213 (1999).*

J.M. Miller, et al., Langmuir, vol. 15, pp. 799-806 (1999).

T. Kimura, et al., Materials Science Forum, vols. 534-536, pp. 1485-1488 (2007).

Korean Office Action as received in the corresponding Korean Patent Application No. 2006-7016590 dated Apr. 14, 2011 with English Translation.

* cited by examiner

PARTICLE-DISPERSED COMPLEX AND SOLID ELECTROLYTIC SENSOR USING IT

TECHNOLOGICAL FIELD

The present invention is related to a particle-dispersed complex in which ruthenium system fine particles are dispersed uniformly in a carbon matrix, and in particular to a very highly active electrochemical catalyst used in an electrode used for a solid electrolyte sensor such as an oxygen sensor, an exhaust gas sensor or the like, or an electrode of an electrochemical device or the like such as an electrolysis or a battery or the like. Further, the present invention is related to a solid electrolyte sensor using the particle-dispersed complex.

PRIOR ART TECHNOLOGY

In an electrochemical reaction with an electrode as a medium, the exchange of charges of material such as ions or the like is carried out at the surface of the electrode, whereby a reaction is accelerated. The electrode used here has a very important role, and in addition to the theoretical decomposition voltage in the electrolytic chemical reaction which is the theoretical energy required for the reaction, excess energy of the electrode characteristic, namely, an overvoltage is required in order to accelerate the targeted electrochemical reaction. This overvoltage is supplied in accordance with the material and state thereof, and because it is the same thing as expressing the so-called catalytic activity, the electrode material is expressed by the term electrochemical catalyst.

In an electrochemical device, the selectivity of reactions by the catalyst and the required excess energy, namely, the overvoltage are very important factors, in the same way as in other chemical reactions. In other words, in an electrochemical sensor, it goes without saying that selectivity is a very important factor, and the overvoltage serves a very important role in the reactivity thereof.

Even with regard to this kind of sensor, even with regard to an electrolytic electrode which participates directly in the electrolytic reaction, or even with regard to a battery electrode which generates electricity by an electrochemical reaction, the activity of the electrochemical catalyst is completely the same, and in the prior art platinum has been used a lot as an electrode having the most activity and stability. In a standard hydrogen electrode, platinum black serves as an electrode and this is defined as zero, and without a doubt platinum is the most known and utilized as effective electrochemical catalyst in the technical field of electrochemistry.

As for platinum group metals other than platinum, these are widely used by themselves as a chemical catalyst, but there has been little use together with carbon as an electrochemical catalyst. Namely, by plating a metal base material with ruthenium by itself or together with a stable metal such as titanium or the like, a so-called insoluble metal electrode in a ruthenium oxide state is used widely as an anode in salt electrolysis. Further, alloys of platinum and platinum group metals other than platinum are used in electrodes for fuel cells. The former is specifically used effectively in creating chlorine gas by oxidizing chlorine ions in an aqueous solution (e.g., see Patent Document 1), and the latter is known to carry out a co-catalytic action (e.g., see Patent Document 2).

Patent Document 1: Japanese Laid-Open Patent Application No. 2002-088494

Patent Document 2: Japanese Laid-Open Patent Application No. 2003-187851

SUMMARY OF THE INVENTION

Problems to be Solved by the Invention

However, as these are mainly used for practical reasons rather than having activity as a catalyst, the sensitivity is dull from the point of reaction characteristics in sensors or the like or in which minute quantity electrochemical reactions or the like are targeted, this has not accorded with goals.

It is an object of the present invention to provide a sensor electrode of a solid electrolyte sensor such as an oxygen sensor, an exhaust gas sensor or the like having good sensitivity even at low temperatures, or a particle-dispersed complex which can form a highly active electrochemical catalyst by dispersing ruthenium system fine particles having a very small particle diameter inside a carbon matrix phase without aggregating, whereby the ruthenium system fine particles form a high catalytic activity state.

Means for Solving the Problems

When the present inventors searched for an electrode of a solid electrolyte sensor having good sensitivity even at low temperature, it was discovered that a particle-dispersed complex having high activity was obtained, in ruthenium system fine particles having a very small particle diameter which were dispersed in a carbon matrix phase without agglutination by carrying on synthesis of a thin film containing ruthenium on a substrate in conditions where there is incomplete oxidation by a CVD method, namely, in the entire carbon substance in which metallic fine particles are dispersed, and this achieved the invention. Namely, the particle-dispersed complex of the present invention is characterized by the fact that fine particles having a particle diameter of 5~100 nm which include ruthenium element as a constituent element are dispersed in a matrix having carbon as a main component, and the complex has electrical conductivity. Further, the particle-dispersed complex of the present invention is characterized by the fact that the case where the entire surface of said fine particles makes contact with at least either said matrix or said fine particles is included. In this regard, the case where said matrix is carbon black or nanocarbon is included. Further, the case where said fine particles are ruthenium metallic fine particles, ruthenium oxide fine particles or surface-oxidized ruthenium metallic fine particles, or a mixture of these fine particles is included. There is high activity because the fine particles have a small particle diameter of 5~100 nm, and there is higher activity if the holding matrix is fine carbon such as carbon black or nanocarbon or the like.

The particle-dispersed complex according to the present invention is preferably held on an electrically conductive substrate. By being held on an electrically conductive substrate, the complex can be shaped so as to be easily utilized for various uses such as a sensor electrode of a solid electrolyte sensor such as an oxygen sensor, an exhaust sensor or the like, or for an electrode or the like of an electrochemical device or the like such as an electrolysis or a battery or the like.

The particle-dispersed complex according to the present invention is preferably formed on a solid electrolyte substrate. In this regard, the case where the interfacial electrical conductivity a between the solid electrolyte substrate and a thin film formed from said particle-dispersed complex formed on the surface of said solid electrolyte substrate is $10^{-6}$ $Sm^{-1}$ or higher and $10^{-2}$ $Sm^{-1}$ or lower at 190~350° C. is included.

Furthermore, the case where the particle-dispersed complex according to the present invention is a sensor electrode of a solid electrolyte sensor or an electrode for a solid electrolyte is included. By forming a particle-dispersed complex on a solid electrolyte substrate, it can be used as an electrode of a fuel cell. At this time, the interfacial resistance between the solid electrolyte and the electrode can be made small even at a low temperature of 190~350° C. In this regard, as a solid electrolyte having oxide ion conductivity, a material in which a stabilizing agent such as calcium oxide or yttrium oxide or the like is dissolved in the state of solid solution in zirconium oxide is generally used as a stabilized zirconium oxide. The solid electrolyte sensor according to the present invention is characterized by the fact that a particle-dispersed complex formed by dispersing fine particles having a particle diameter of 5~100 nm which include ruthenium element as a constituent element in a matrix having carbon as a main component and having electrical conductivity is formed as an electrode on the surface of a zirconium oxide substrate which includes a stabilizing agent. Further, the solid electrolyte sensor according to the present invention includes the case where the entire surface of said fine particles makes contact with at least either said matrix or said fine particles.

The case that the particle-dispersed complex according to the present invention can be an electrochemical catalyst is included. It can be used for electrolysis or as an electrode of an electrochemical device such as a battery or the like. Furthermore, it can be used as a catalyst for various reactions such as hydrogenation reactions of aromatic rings, aniline or pyridine, oxidation reactions, dehydrogenation reactions, decomposition reactions, oxo reactions, isomerization reactions, hydrocracking and reforming reactions.

Effect of the Invention

In the particle-dispersed complex according to the present invention, because ruthenium system fine particles having a very small particle diameter are dispersed in a carbon matrix phase without aggregation, the ruthenium system fine particles are in a high catalytic activity state. Further, it forms an electrode for a solid electrolyte sensor such as an oxygen sensor, exhaust gas sensor or the like having good sensitivity even at low temperature, or an electrochemical catalyst having high activity.

DESCRIPTION OF SYMBOLS

Figure 1:
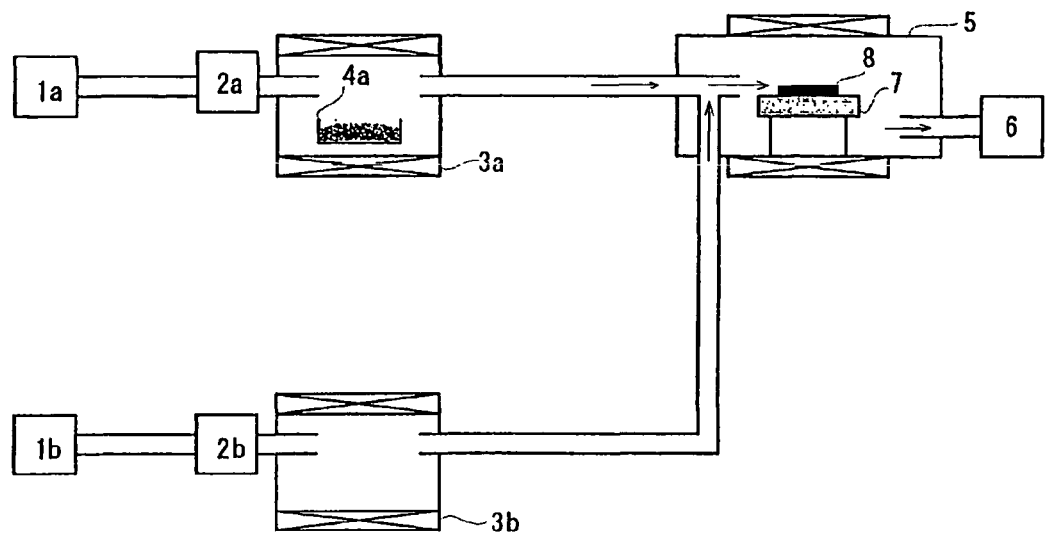
FIG. 1 is a conceptual drawing showing one embodiment of a CVD manufacturing apparatus used in forming an electrode film made from a particle-dispersed complex according to an example of the present invention.

1*a*: inert gas generating source
1*b*: oxygen gas generating source
2: gas flow controller
3*a*: source material supply pipe
3*b*: gas heating pipe
4*a*: source material container
5: reaction chamber
6: exhaust means
7: substrate holding portion
8: substrate Preferred Embodiments of the Invention The present invention is described in detail below with reference to preferred embodiments, but it should not be interpreted that the present invention is limited to these descriptions.

Using the CVD film forming apparatus shown in FIG. 1, a film of a particle-dispersed complex according to the present invention was formed on a substrate. The manufacturing apparatus of FIG. 1 is an example. This CVD film forming apparatus is equipped with gas generating sources 1*a*, 1*b* for an inert gas and oxygen gas, gas flow controllers 2*a*, 2*b*, a source material supply pipe 3*a* equipped with a heating portion, a gas heating pipe 3*b* equipped with a heating portion, a source material container 4*a*, a reaction chamber 5 equipped with a heating portion, exhaust means 6, and a substrate holding portion 7.

First, a description will be given for the manufacturing apparatus of FIG. 1. The gas generating source 1*a* supplies an inert gas which is a carrier gas. The gas generating source 1*b* supplies oxygen gas. The gas flow controller 2*a* controls the carrier gas flow required for the source gas supply pipe 3*a* when an inert gas such as argon or nitrogen gas or like generated by the gas generating source 1*a* is supplied to the source material supply pipe 3*a*. The source material supply pipe 3*a* is equipped with a heating portion, and the source material container 4*a* provided inside and a source material placed in this are heated and vaporized, whereby a source material is supplied together with a carrier gas to the inside of the reaction chamber 5. At the same time, oxygen gas generated by the gas generating source 1*b* is heated by the gas heating pipe 3*b* and supplied to the inside of the reaction chamber 5. The inside the reaction chamber 5 undergoes pressure reduction to a prescribed pressure by the exhaust means 6. A substrate 8 is placed on the substrate holding portion 7 provided in the reaction chamber 5, and the substrate 8 is heated to a prescribed temperature by the heating portion of the reaction chamber 5.

As for the source material, a ruthenium organometallic compound or a ruthenium organometallic complex or the like is used. In this regard, ruthenium dipivaloylmethanate is preferred as an organometallic complex, and these source materials are put in the source material container 4a, and the source material container 4a is placed inside the source material supply pipe 3a.

A dipivaloylmethanate complex belongs to a β-diketone complex (R1-CO—$CH_2$—CO—R2). For example, compared with ruthenium dipivaloylmethanate ($Ru(dpm)_3$), ruthenium acetylacetonate ($Ru(acac)_3$) which belongs to the same β-diketone complex requires a high heating temperature in order to obtain the required vapor pressure. In this regard, in the case of ruthenium dipivaloylmethanate, the heating temperature for carrying out vaporization can be set lower than that for ruthenium acetylacetonate, and there is almost no residue after vaporization. Accordingly, the utilization efficiency of the source material becomes high.

In the present invention, when ruthenium dipivaloylmethanate is synthesized by reacting ruthenium trichloride and dipivaloylmethane under the presence of an alkaline reaction accelerating agent, a raw source material is obtained by reflux under a nitrogen atmosphere, and such raw source material is refined by a column chromatography method, and the use of ruthenium dipivaloylmethanate refined by sublimation is even more preferred. As for the ruthenium dipivaloylmethanate obtained by the manufacturing method described above, oxidation decomposition does not occur during synthesis due to reflux under a nitrogen atmosphere, and the byproduct content is small. Accordingly, the vaporization efficiency is high and there is little residue after vaporization. Further, because the byproduct content is small, decomposition before reaching the substrate is reduced, and ruthenium dipivaloylmethanate still having a high purity is supplied to the substrate surface. Furthermore, because there is little foreign matter gas such as partial decomposition byproducts of the source material, carbonaceous compounds or the like, for example, created by the decomposition of ruthenium dipivaloylmethanate, reactions at the substrate surface proceed homogeneously, whereby it becomes possible to deposit a thin film formed from particles having a uniform particle diameter.

As for the reflux conditions, under a nitrogen atmosphere they are 100~230° C., and preferably 120~210° C., and 15~25 hours, and preferably 18~22 hours, for example. Further, as an alkaline reaction accelerating agent, sodium hydrogen carbonate, potassium hydrogen carbonate or the like, for example, can be shown as examples.

As for a source material dish which is the source material container 4a, a dish made of an inert material for each organometallic complex is selected, such as a quartz boat, for example.

Further, in FIG. 1 a description was given for a method of subliming a dipivaloylmethanate complex, but a dipivaloylmethanate complex may be dissolved in an organic solvent such as ethanol, for example, and put into a vaporization container, and then source material vapor may be introduced into the reaction chamber 5 by bubbling.

A description will be given for the process of forming a film with the particle-dispersed complex according to the present invention on a substrate using the CVD film forming apparatus shown in FIG. 1. The inside of the reaction chamber 5 is set at a prescribed pressure by the exhaust means 6. The pressure is set at 13~4000 Pa, and preferably 13~1000 Pa.

The reaction chamber 5 is heated, and the substrate 8 placed on the substrate holding portion 7 is heated to a prescribed temperature. As for the substrate temperature, heating is carried out at a temperature required for a decomposition reaction of the source material compound at the surface.

The substrate is suitably selected in accordance with the purpose, and a conductive substrate such as metal, carbon, conductive ceramic or the like are shown as examples. A quartz glass substrate is also fine. In the present embodiment, in order to describe as an example the case where it is used as an electrode for a solid electrolyte, the substrate is made a solid electrolyte, for example, a solid electrolyte substrate having oxide ion conductivity formed from zirconium oxide containing a stabilizer. The stabilizer is preferably a metal oxide such as magnesium oxide, calcium oxide, yttrium oxide, scandium oxide or cerium oxide or the like. The zirconium oxide containing a stabilizer is a stabilized zirconium oxide (stabilized zirconia) or a partially stabilized zirconium oxide (partially stabilized zirconia).

Next, the source material supply pipe 3a is heated, and the source material inside the source material container 4a is heated. The source material heating temperature is made 140~270° C. The source material heating temperature is suitably adjusted in order to obtain a desired vaporization rate.

Next, an inert gas from the gas generating source 1a, for example, argon gas or nitrogen gas is supplied to the source material supply pipe 3a via the gas flow controller 2a. Further, oxygen gas from the gas generating source 1b is supplied to the gas heating pipe 3b via the gas flow controller 2b. The oxygen gas is heated by the gas heating pipe 3b in order to match the temperature of the carrier gas of the source material. The inert gas containing the vaporized source material and the oxygen gas may be introduced separately into the inside of the reaction chamber, or as shown in FIG. 1, in order to more reliably carry out mixing of the inert gas containing the vaporized source material and the oxygen gas, they may be mixed and supplied directly before introduction to the substrate. In this regard, the flow of inert gas supplied to the source material supply pipe 3a and the heating temperature of the source material are respectively adjusted in order to control the composition of the film to be obtained.

The mixture gas of the inert gas and the oxygen gas forms at least a carrier gas which guides the source material gas to the substrate inside the reaction chamber, and the flow of this carrier gas is suitably adjusted in accordance with the size of the reaction chamber 5 and the size of the substrate. In this regard, the oxygen content percent in the carrier gas which is the mixture gas of the inert gas and the oxygen gas is preferably made 9% or higher in order to obtain crystalline fine particles. Further, in order to obtain amorphous fine particles, the oxygen content percent in the carrier gas is preferably made less than 9%.

The inert gas containing the vaporized source material and the oxygen gas are sent to the inside of the reaction chamber 5, and introduced to the heated substrate surface. Further, because the reaction chamber 5 is set at a higher temperature than the source material supply pipe and the pipeline reaching the reaction chamber, there is no condensation/solidification of the source material partway. Furthermore, by using a ruthenium dipivaloylmethanate having a prescribed high purity, lowering of the source material utilization efficiency due to the progression of side reactions and the like during conveyance of the source material is suppressed, and source material decomposition proceeds homogeneously on the solid electrolyte substrate, whereby a roughly uniform thin film fine structure is obtained.

The source material that reaches the substrate surface is heat decomposed under a prescribed oxygen content percent, and a particle-dispersed complex is deposited on the substrate. This particle-dispersed complex is formed from a matrix in which carbon contained in a ruthenium organometallic complex forms the main component, and fine particles which are dispersed in the matrix having a particle diameter of 5~100 nm, or preferably a particle diameter of 5~50 nm, or more preferably a particle diameter of 5~20 nm of ruthenium element contained in the ruthenium organometallic complex as a constituent element. As described above, either crystalline fine particles or amorphous fine particles are obtained depending on the oxygen content percent in the carrier gas. It is preferred that the entire surface of the fine particles makes contact with at least either the matrix or the fine particles, namely, there are almost no or absolutely no holes or gaps in the interface between the fine particles and the matrix. By the bonding between the fine particles and the matrix on the entire surface of the interface thereof, and in combination with the fact that the particle diameter of the dispersed fine particles is small, the interfacial surface area making contact becomes very large, and as a result, the particle-dispersed complex is believed to obtain a high interfacial electrical conductivity. Further, as for the dispersion state in the matrix of the particle-dispersed complex, it is preferred that there is uniformly dispersing without aggregation. Namely, it is more preferred that the entire surface of the fine particles makes contact with only the matrix. This is because the interfacial surface area in which the matrix makes contact becomes large.

This particle-dispersed complex has conductivity. Further, the matrix contains carbon black or nanocarbon.

The crystalline fine particles change in accordance with the oxygen content percent in the carrier gas, and when the oxygen content percent is 9% or higher, ruthenium metallic fine particles, surface-oxidized ruthenium metallic fine particles, or ruthenium oxide fine particles are obtained respectively in ascending order of the oxygen content percent. As described in the present example, specifically by setting conditions in which the oxygen content percent of the carrier gas is greater than 9% and less than 23% and the temperature of the substrate is 350~450° C., it is possible to disperse ruthenium metallic fine particles as crystalline fine particles in a matrix having carbon as a main component.

In the particle-dispersed complex according to the present embodiment, the atomic number ratio of carbon and ruthenium is preferably set at (10:90)~(90:10), and more preferably set at (30:70)~(70:30). Furthermore, it is preferably set at (50:50)~(65:35). When carbon is smaller than (10:90) in the atomic number ratio, aggregation of the fine particles occurs, on the other hand, when carbon is greater than (90:10) in the atomic number ratio, the dispersion concentration of the fine particles is small, and there are disadvantageous cases such as that where the response rate of an oxygen sensor becomes slow, or that where the electromotive force/limiting current become small, or the like. However, in this case, by creating an analytical curve in advance, it can be used to determine the oxygen concentration. This composition can be controlled freely by the vaporization temperature of the source material, the carrier gas flow and the like.

In the case where the particle-dispersed complex according to the present embodiment is used as an electrode for a solid electrolyte, an increase of the interfacial resistance of the solid electrolyte substrate—electrode is suppressed even at a low temperature range, such as 190~350° C., for example. This includes the cases where the interfacial electrical conductivity σ between the solid electrolyte substrate and the thin film formed from the particle-dispersed complex formed on the surface of such solid electrolyte substrate is greater than or equal to $10^{-6}$ $Sm^{-1}$ at 190° C., and greater than or equal to $10^{-6}$ $Sm^{-1}$ and less than or equal to $10^{-2}$ $Sm^{-1}$ at 190~350° C.

The substrate forming this electrode is particularly suited as a sensor electrode of an oxygen sensor or the like, a structural member of a fuel cell, and an electrode for electrolysis. Further, in the case of being used as a catalyst, a ruthenium catalyst shows high activity in the hydrogenation of rings of aliphatic carbonyl compounds and aromatic compounds, and under mild conditions, hydrogenation can be carried out without accompanying side reactions. In particular, when water coexists in the reaction system, the catalyst works as a catalyst together with water and displays a high activity. Further, the catalyst has exceptional toxin resistance to sulfur compounds in spite of belonging to a precious metal catalyst. Furthermore, it is very stable in acids and bases, and it can be used even in reactions in strong acids. In addition to that, in the present embodiment, an electrolytic reaction occurs at low temperature, wherein the decomposition and the reaction occurs due to electrolysis. Further, electricity would be generated according to the decomposition. Furthermore, because the ruthenium system fine particles are dispersed in the condition of fine particles, there are characteristics such as (1) the activity is high even when a very small amount of catalyst is used, (2) because a reaction can be carried out under mild conditions, it cost less for utility and equipment investment, (3) because selectivity is good, there is no lowering of the yield due to side reactions, and (4) it is possible to use a solvent that is either acidic or basic.

Further, as for the thickness of the electrode, the optimum film thickness depends on the electrode shape and the size thereof and the like of a solid electrolyte oxygen sensor or a solid electrolyte fuel cell, and is set at 100 nm ~200 μm, for example. As in the examples described later, the film thickness may be 1 μm or less. The film thickness can be controlled depending on conditions such as the amount of supplied source material and the film formation time and the like.

EXAMPLES (Source Material Vaporization Test)

Figure 2:
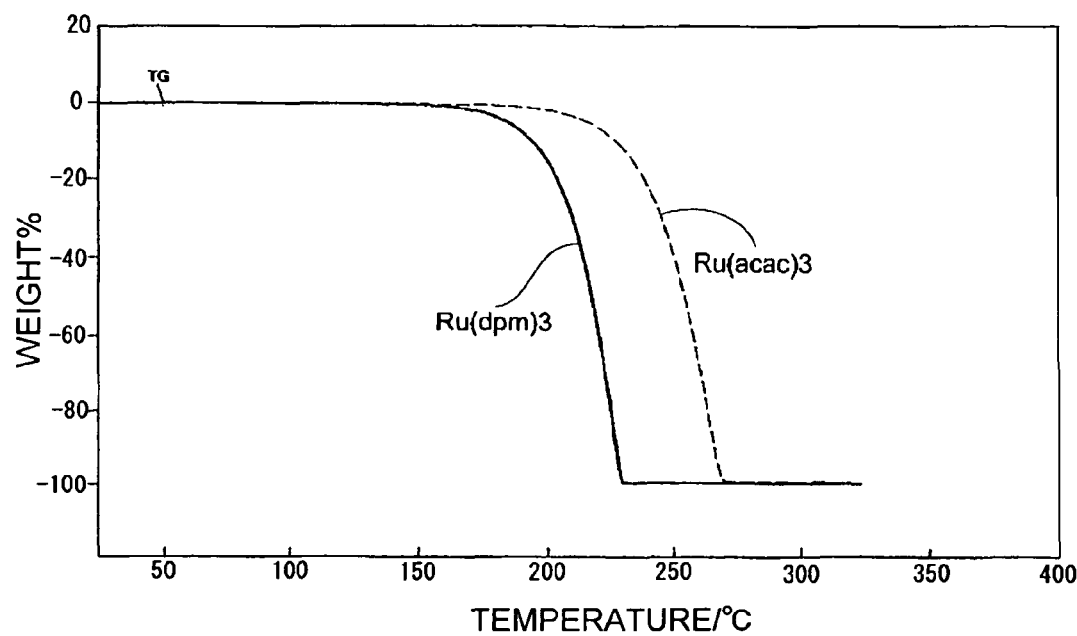
FIG. 2 is a drawing which shows thermogravimetric curves of source materials, and the two examples $Ru(dpm)_3$ and $Ru(acac)_3$ are shown.

When ruthenium dipivaloylmethanate was synthesized by reacting ruthenium trichloride and dipivaloylmethane under the presence of an alkaline reaction accelerating agent, a raw source material was obtained by reflux for 20 hours under a nitrogen atmosphere within the range 155~200° C., and such raw source material was refined by a column chromatography method, and then with ruthenium dipivaloylmethanate refined by sublimation as an example, a thermogravimetric analysis was carried out. The results are shown in FIG. 2. As is clear from the thermogravimetric curve, sublimation began from around 140° C., and sublimation was complete at around 230° C. On the other hand, when the same sublimation test was carried out with ruthenium acetylacetonate (Ru(acac)$_3$) as a reference example, sublimation began from around 200° C., and sublimation was complete at around 270° C. The results are shown in FIG. 2 in the same manner. Accordingly, ruthenium dipivaloylmethanate has a higher vapor pressure characteristic than ruthenium acetylacetonate at a low temperature. Further, because the vaporization stability is good, there is little residue. This suggests that ruthenium dipivaloylmethanate is stable and can reach the substrate.

Experiment 1

Using the apparatus of FIG. 1, the formation of an electrode from a particle-dispersed complex according to the present embodiment on an yttria stabilized zirconium oxide substrate was carried out. A prescribed amount of oxygen was mixed in argon, and ruthenium dipivaloylmethanate was introduced into the inside of the reaction chamber. At this time, argon was set at 20 sccm, and the oxygen gas flow was set at 10 sccm. Accordingly, the oxygen content percent of the carrier gas is 33%. The film formation pressure was 400 Pa. The substrate temperature was 400° C. The film formation time was adjusted to obtain a film thickness of 400 nm. This was made Example 1.

Experiment 2

Except for the oxygen gas flow being set at 8 sccm, a film was formed under the same conditions in Experiment 1, and this was made Example 2. The oxygen content percent of the carrier gas is 29%.

Experiment 3

Except for the oxygen gas flow being set at 6 sccm, a film was formed under the same conditions in Experiment 1, and this was made Example 3. The oxygen content percent of the carrier gas is 23%.

Experiment 4

Except for the oxygen gas flow being set at 4 sccm, a film was formed under the same conditions in Experiment 1, and this was made Example 4. The oxygen content percent of the carrier gas is 17%.

Experiment 5

Except for the oxygen gas flow being set at 2 sccm, a film was formed under the same conditions in Experiment 1, and this was made Example 5. The oxygen content percent of the carrier gas is 9%.

Experiment 6

Except for the oxygen gas flow being set at 0 sccm, a film was formed under the same conditions in Experiment 1, and this was made Example 10. The oxygen content percent of the carrier gas is 0%.

Experiment 7

Except for the oxygen gas flow being set at 4 sccm and the substrate temperature being set at 350° C., a film was formed under the same conditions in Experiment 1, and this was made Example 6. The oxygen content percent of the carrier gas is 17%.

Experiment 8

Except for the oxygen gas flow being set at 4 sccm and the substrate temperature being set at 450° C., a film was formed under the same conditions in Experiment 1, and this was made Example 7. The oxygen content percent of the carrier gas is 17%.

Experiment 9

Except for the oxygen gas flow being set at 4 sccm and the substrate temperature being set at 500° C., a film was formed under the same conditions in Experiment 1, and this was made Example 8. The oxygen content percent of the carrier gas is 17%.

Experiment 10

Except for the oxygen gas flow being set at 4 sccm and the substrate temperature being set at 550° C., a film was formed under the same conditions in Experiment 1, and this was made Example 9. The oxygen content percent of the carrier gas is 17%.

Experiment 11

Except for the oxygen gas flow being set at 4 sccm and the substrate temperature being set at 600° C., a film was formed under the same conditions in Experiment 1, and this was made Example 11. The oxygen content percent of the carrier gas is 17%.

Experiment 12

Except for the oxygen gas flow being set at 4 sccm and the substrate temperature being set at 300° C., a film was formed under the same conditions in Experiment 1, and this was made Comparative Example 1. The oxygen content percent of the carrier gas is 17%.

(Evaluation by X-Ray Diffraction)

Identification of the phase was carried out by an XRD (Rigaku Geigerflex). Phase changes due to oxygen content percent under conditions where the substrate temperature is 400° C. were examined. The results are shown in FIG. 3.

Further, phase changes of the case where the substrate temperature is changed under the conditions where the oxygen gas flow is 4 sccm, namely, where the oxygen content percent of the carrier gas is 17% were examined. The results are shown in FIG. 4.

Figure 3:
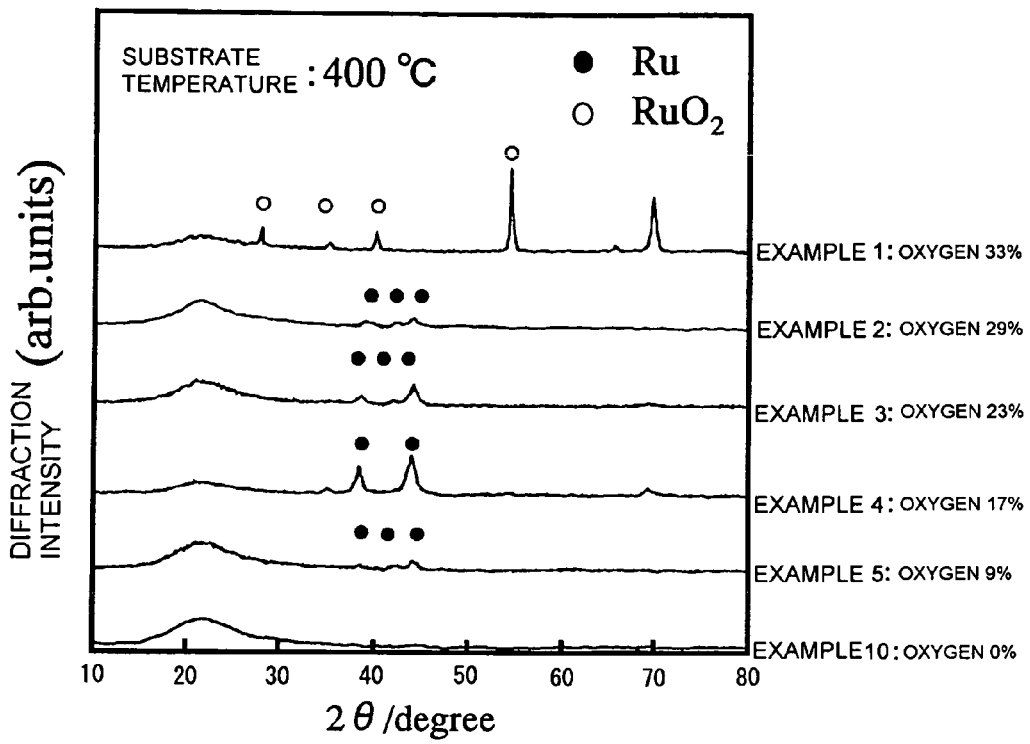
FIG. 3 is an XRD chart showing phase changes due to the oxygen content percent under conditions where the substrate temperature is 400° C.

First, reference is made to FIG. 3 which shows the changes of the crystalline phase as the oxygen content percent in the carrier gas is changed with the substrate temperature fixed at 400° C. In Example 10 where the oxygen content in the carrier gas is 0%, the matter obtained by deposition on the substrate was amorphous, and amorphous particles were dispersed inside a carbon matrix. In Example 5 where the oxygen content in the carrier gas is 9%, peaks of metallic ruthenium crystals were observed, and in Example 4 where the oxygen content in the carrier gas is 17%, peaks of metallic ruthenium crystals having better crystallinity were observed. Further, in Example 3 where the oxygen content in the carrier gas is 23% and in Example 2 where the oxygen content in the carrier gas is 29%, peaks of metallic ruthenium crystals were observed, but the crystallinity of Example 4 was better. In this regard, it is presumed that the crystallinity is lowered by the oxidizing of the surface of the ruthenium metallic fine particles. Further, in Example 1 where the oxygen content in the carrier gas is 33%, peaks of ruthenium oxide crystals having good crystallinity were observed. Accordingly, it was understood that a deposition containing ruthenium system crystals having crystallinity is obtained by setting the oxygen content percent at 9% or higher.

Figure 4:
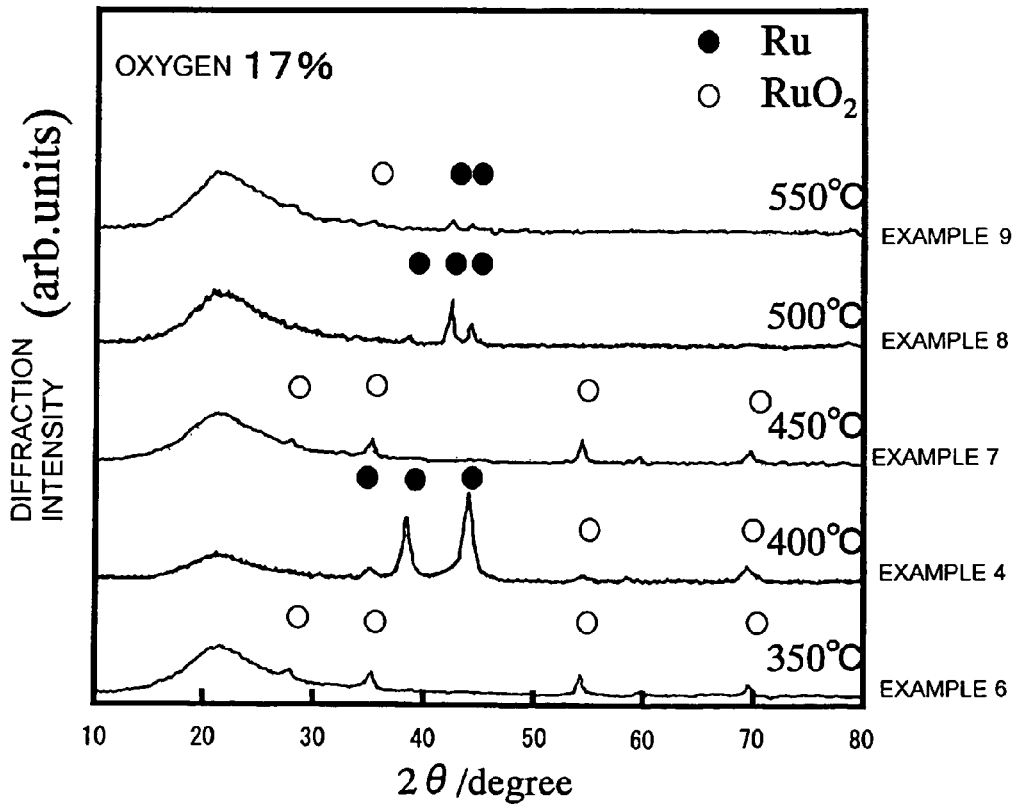
FIG. 4 is an XRD chart showing phase changes of the case where the substrate temperature is changed under conditions where the oxygen content percent of the carrier gas is 17%.

Next, reference is made to FIG. 4 which shows the changes of the crystalline phase as the substrate temperature is changed with the oxygen content percent in the carrier gas fixed at 17% where ruthenium metallic crystals having good crystallinity are deposited. In Example 6 where the substrate temperature is 350° C., peaks of ruthenium oxide crystals were observed, and in Example 4 where the substrate temperature is 400° C., peaks of metallic ruthenium crystals having good crystallinity were observed. Further, in Example 7 where the substrate temperature is 450° C., peaks of ruthenium oxide crystals were observed. In Example 8 where the substrate temperature is 500° C., peaks of metallic ruthenium crystals were observed. In Example 9 where the substrate temperature is 550° C., peaks of metallic ruthenium crystals having a low crystallinity compared to Example 4 were observed. When Example 4 and Examples 6~9 are compared, in the case where the substrate temperature is different at the same oxygen content percent, the crystalline phase obtained in accordance with the substrate temperature is different, and Example 4 obtained a deposition having the best crystallinity. Further, in the case where film formation is carried out at 300° C. in Comparative Example 1, a deposition was not obtained. It is believed the source material gas did not decompose. Further, in the case where film formation was carried out at 600° C. in Example 11, an amorphous particle-dispersed complex was obtained.

(Fine Structure Evaluation)

Figure 5:
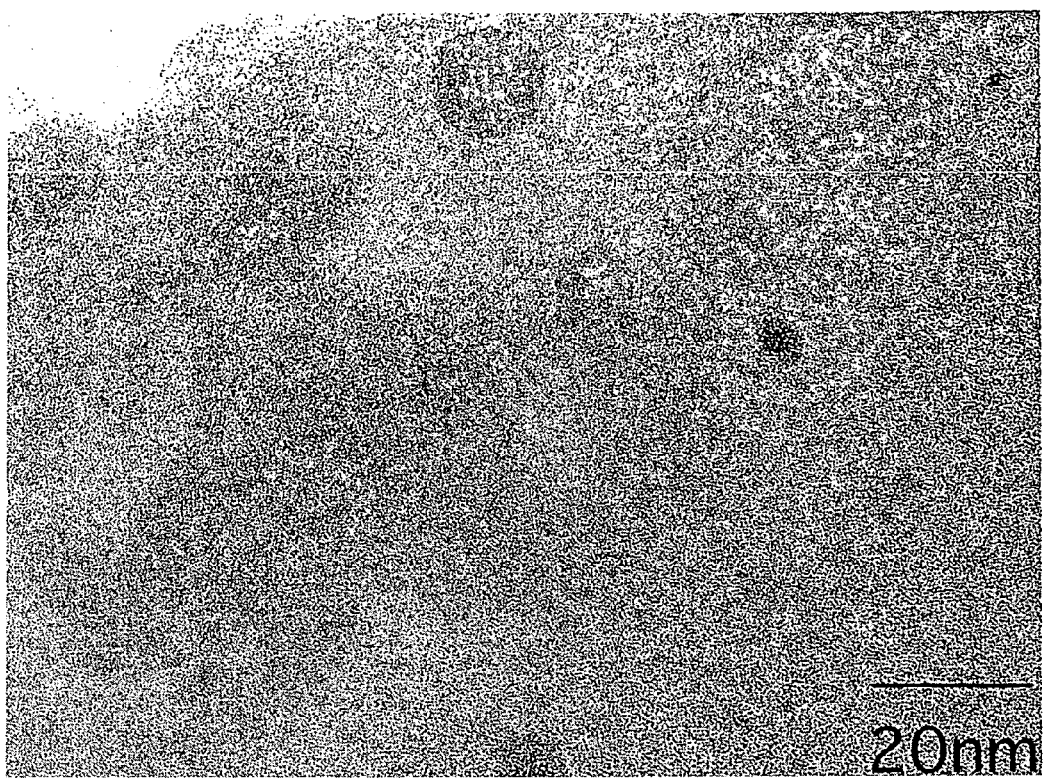
FIG. 5 is a drawing (photographic image) showing an electron microscope photograph of a TEM observation of Example 4.

Next, in Example 4 having the best crystallinity, observation of fine structure was carried out by a transmission electron microscope (TEM, JEOL-JEM-ARM1250). The results of the TEM observations of Example 4 are shown in FIG. 5. In FIG. 5, it was understood that spherical fine particles having a diameter of approximately 5~20 nm are dispersed without aggregation. As for these spherical particles, a lattice arrangement was observed in FIG. 5, and these are believed to be roughly monocrystal fine particles. Further, when the results of X-ray diffraction are considered, the spherical fine particles are believed to be metallic ruthenium fine particles. At the interface of the particles and the matrix, holes and gaps were not observed. Further, it was understood that the matrix holding these fine particles is a matrix in which carbon derived from the source material is made a main component. This carbon matrix is an aggregate of carbon black or a so-called nanocarbon. Accordingly, the sample of Example 4 is a particle-dispersed complex, and is formed from a matrix in which carbon contained in a ruthenium organometallic complex is made a main component, and fine particles having a particle diameter of 5~20 nm which include ruthenium element contained in a ruthenium organometallic complex as a constituent element dispersed in the matrix.

In the X-ray diffraction pattern of Example 4, the Scherrer Method was used, and the estimated crystallite size from the half width of the Ru diffraction peak was approximately 8 nm.

(Evaluation of Electrical Characteristics)

The deposition of Example 4 is believed to have a very high activity because ruthenium fine particles resembling spherical monocrystals are dispersed. In this regard, a lead wire was attached to the surface of the sample of Example 4, and evaluation of the complex impedance was carried out by an alternating current impedance method.

Figure 6:
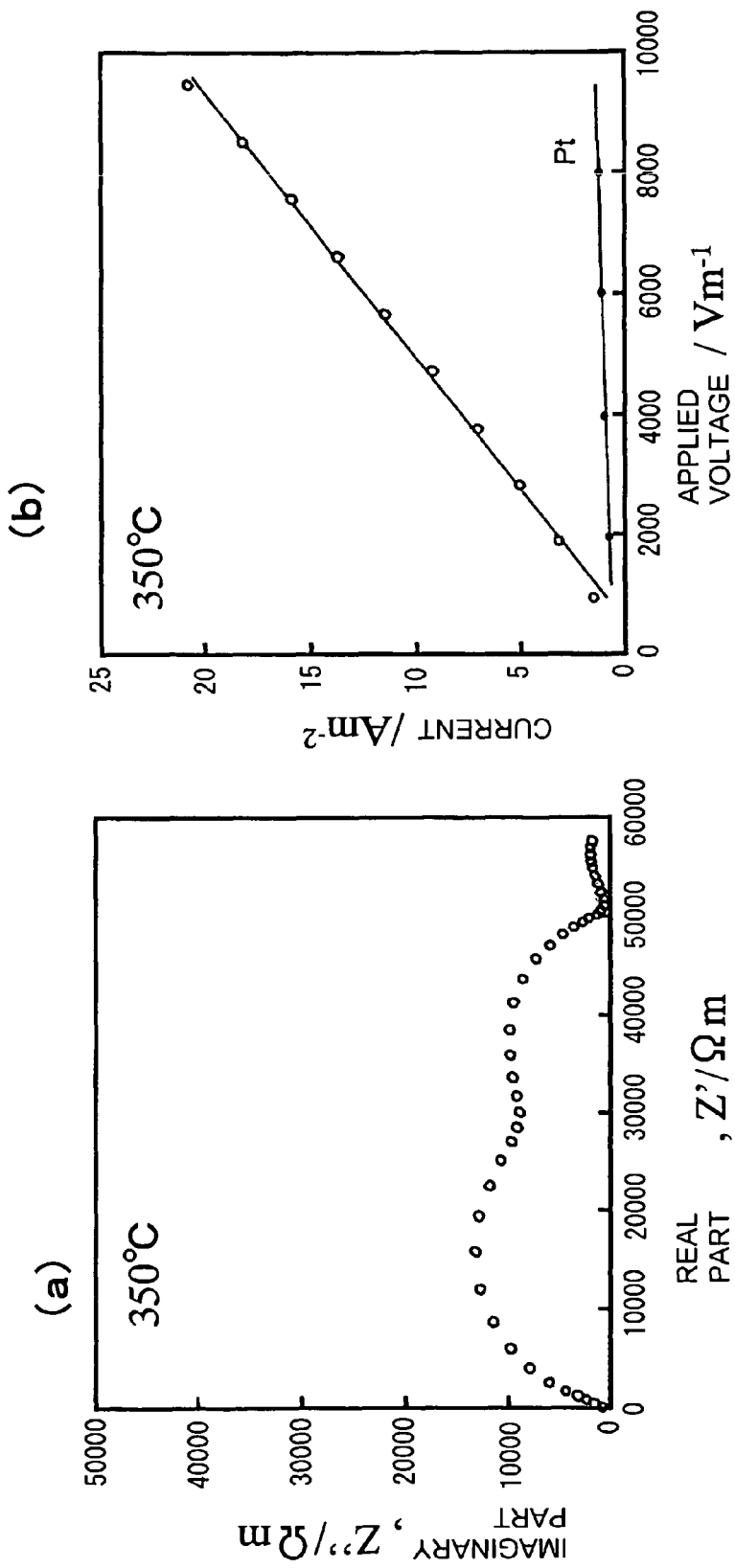
FIG. 6(*a*) is a Cole-Cole plot of Example 4 at 350° C., and FIG. 6(*b*) shows the measurement results of the current-voltage characteristics by a direct current method.
Figure 7:
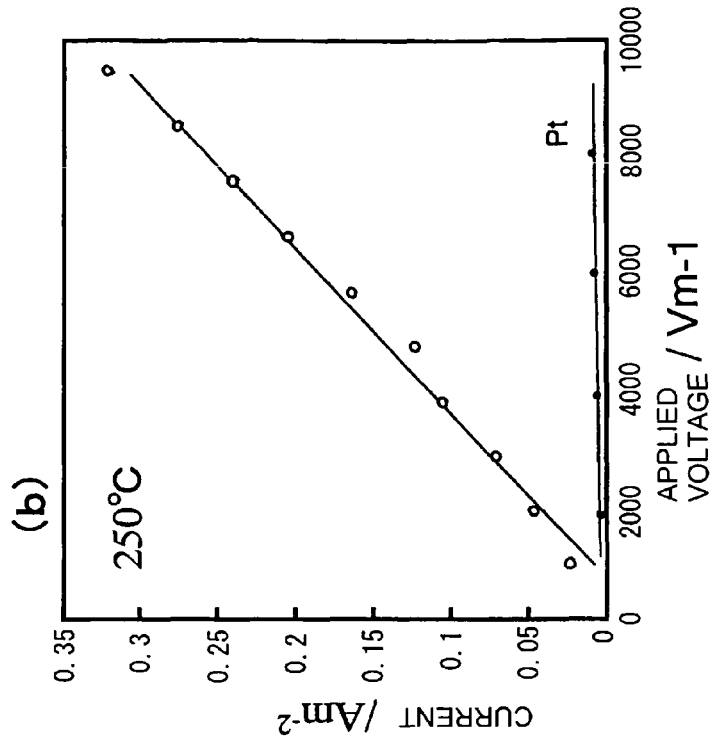
FIG. 7(*a*) is a Cole-Cole plot of Example 4 at 250° C., and FIG. 7(*b*) shows the measurement results of the current-voltage characteristics by a direct current method.
Figure 7:
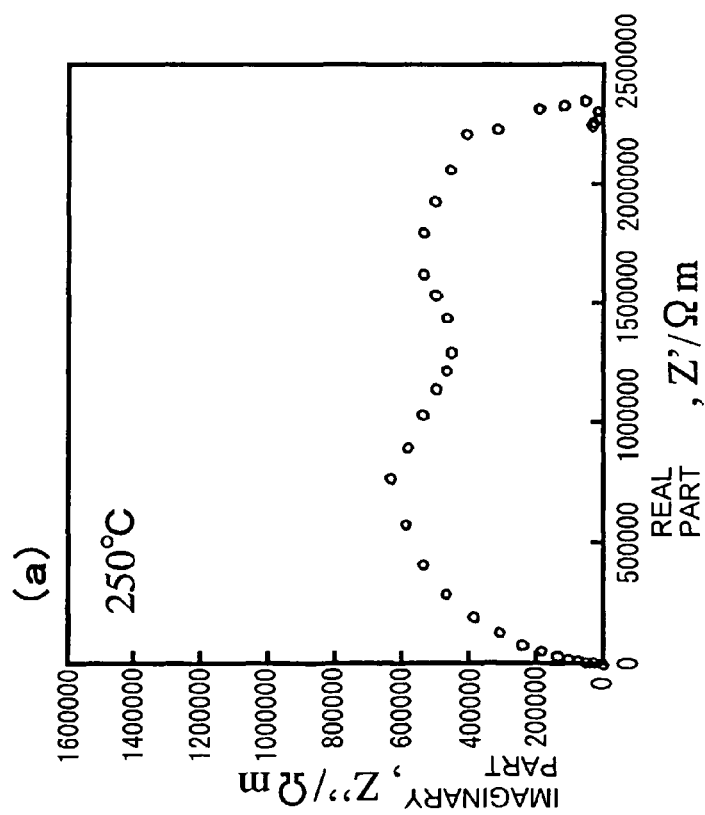
Figure 8:
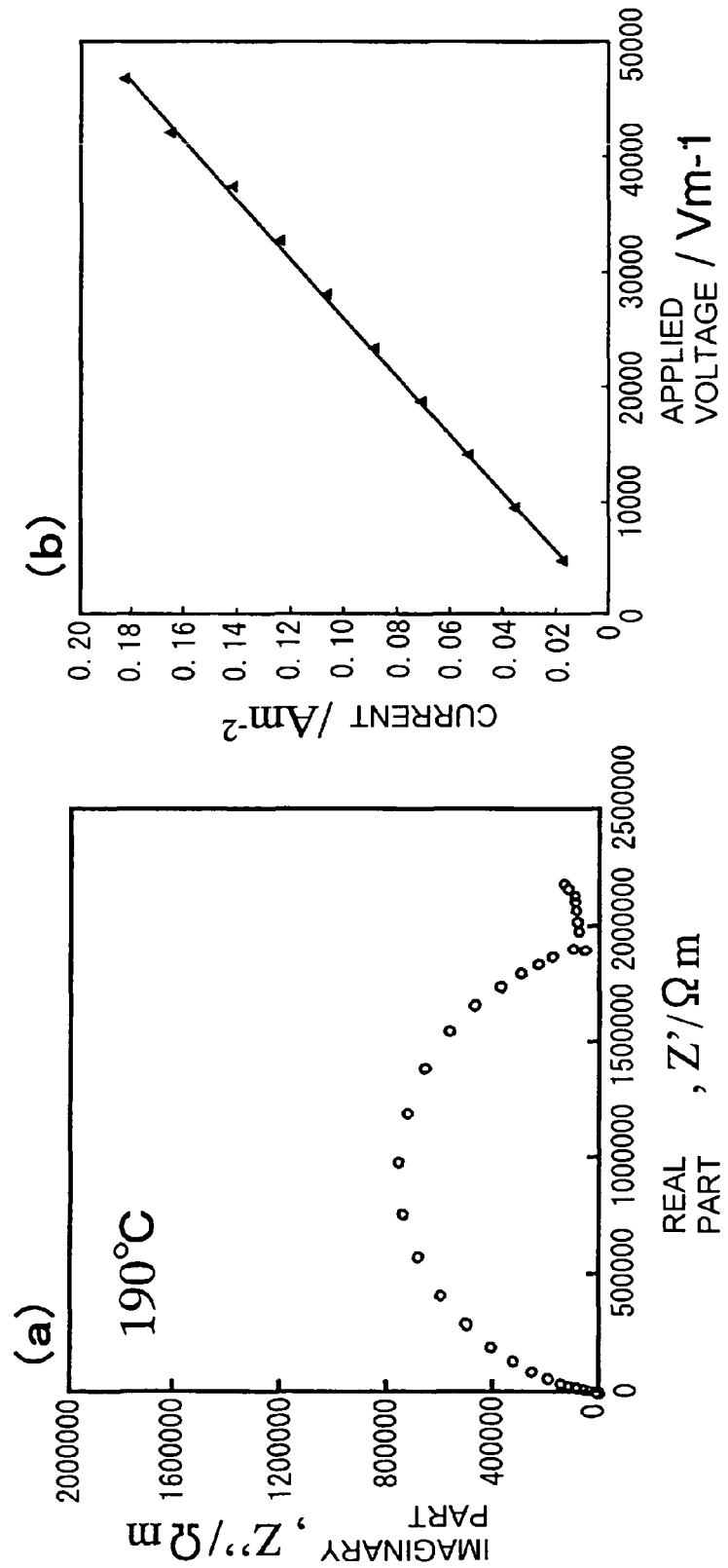
FIG. 8(*a*) is a Cole-Cole plot of Example 4 at 190° C., and FIG. 8(*b*) shows the measurement results of the current-voltage characteristics by a direct current method.

A Cole-Cole plot at 350° C. of Example 4 is shown in FIG. 6(*a*), and measurement results of the current-voltage characteristics by a direct current method are shown in FIG. 6(*b*). A Cole-Cole plot at 250° C. of Example 4 is shown in FIG. 7(*a*), and measurement results of the current-voltage characteristics by a direct current method are shown in FIG. 7(*b*). Further, a Cole-Cole plot at 190° C. of Example 4 is shown in FIG. 8(*a*), and measurement results of the current-voltage characteristics by a direct current method are shown in FIG. 8(*b*). Further, FIGS. 6~8 which are data in which 350° C., 250° C. and 190° C. are made measurement temperatures are shown as representative examples.

For example, the three semicircles of the Cole-Cole plot shown in FIG. 6(*a*) correspond to, from the low impedance side, the transgranular resistance of the solid electrolyte (namely, resistance of the bulk solid electrolyte), intergranular resistance of the solid electrolyte, and the interfacial resistance of the solid electrolyte and the electrode film. The intercepts of the real axes are resistance values. However, depending on the measurement conditions, there are situations where only a part of the three semicircles can be seen. In particular, there are cases where the measurement of the interfacial resistance is difficult. Accordingly, the current-voltage characteristics are measured by a direct current method, and the direct current resistance value is obtained from the slope thereof. Because the direct current resistance value corresponds to the total resistance value of the three semicircles, the interfacial resistance value was calculated by subtracting the bulk resistance and the intergranular resistance which can be measured by an alternating current impedance method from the total resistance. In order to make the accuracy of this method clear, when confirmation was carried out by a sample such as that exhibiting the three semicircles, it was confirmed that the experimental results matched well.

Figure 9:
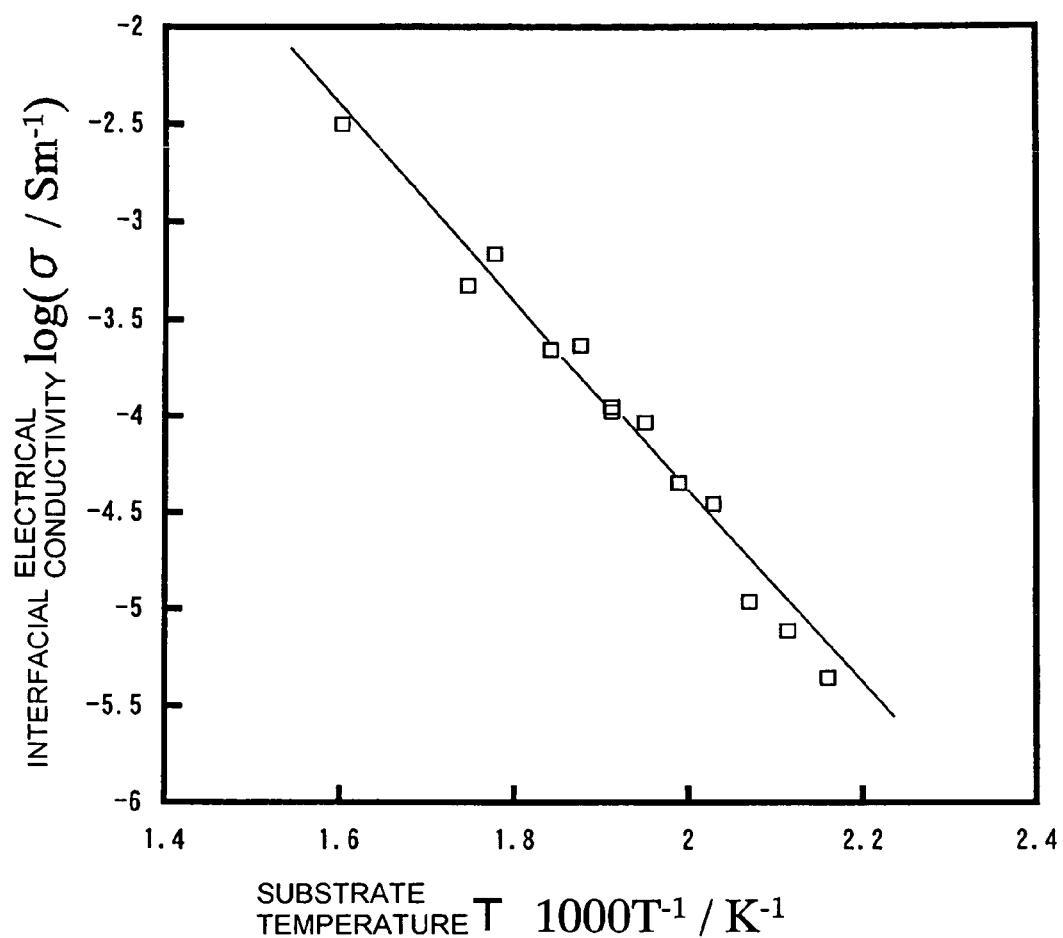
FIG. 9 shows the temperature changes of the interfacial electrical conductivity of Example 4 at 190~350° C.

As shown in the graphs of FIGS. 6~8, in the sample of Example 4, it was understood that it is possible to carry out measurements of the resistance value in the temperature range 190~350° C. which is a very low temperature for an electrode for a solid electrolyte. In this regard, the temperature changes of the interfacial electrical conductivity in the temperature range 190~350° C. which includes the measurement temperatures 350° C., 250° C. and 190° C. are shown in FIG. 9. The interfacial electrical conductivity σ at 350° C. was $3.2 \times 10^{-3}$ $Sm^{-1}$, and the interfacial electrical conductivity a at 190° C. was $7.9 \times 10^{-6}$ $Sm^{-1}$. Further, as shown in FIG. 9, when the substrate temperature T(K) is set in the temperature range 190~350° C., it was understood that there is good correlation between 1000/T and the interfacial electrical conductivity $\log(\sigma/Sm^{-1})$, and this is shown by a roughly straight line.

The interfacial electrical conductivity corresponds to the charge-transfer reaction rate in a three-phase interface of gas/electrode/solid electrolyte. The particle-dispersed complex of Example 4 shows an interfacial electrical conductivity which is 10,000~100,000 times higher compared to a Pt electrode.

From this fact, the particle-dispersed complex of Example 4 can be said to have a very low interfacial resistance at low temperature as an electrode for a solid electrolyte. As shown in FIG. 5, since there are almost no holes or gaps in the interface of the dispersed particles and the matrix, the dispersed particles and the matrix bond each other over the entire surface of the contacting interfacial surface area is very large. Further, because the dispersion state of the particle-dispersed complex in the matrix was uniformly dispersed without aggregation, there is very little contact between particles, and the interfacial surface area where the particles and the matrix make contact is large. As a result, it is believed that the particle-dispersed complex obtains a high interfacial electrical conductivity. Accordingly, when the particle-dispersed complex of Example 4 is used as an electrode of a solid electrolyte oxygen sensor, the sensitivity is good and current can be detected even at a low temperature, whereby the accuracy is high. Further, when a fuel cell is operated at low temperature, it is understood that Example 4 is suitable as an electrode which is very sensitive to oxygen ion conduction and has a rapid response.

Figure 10:
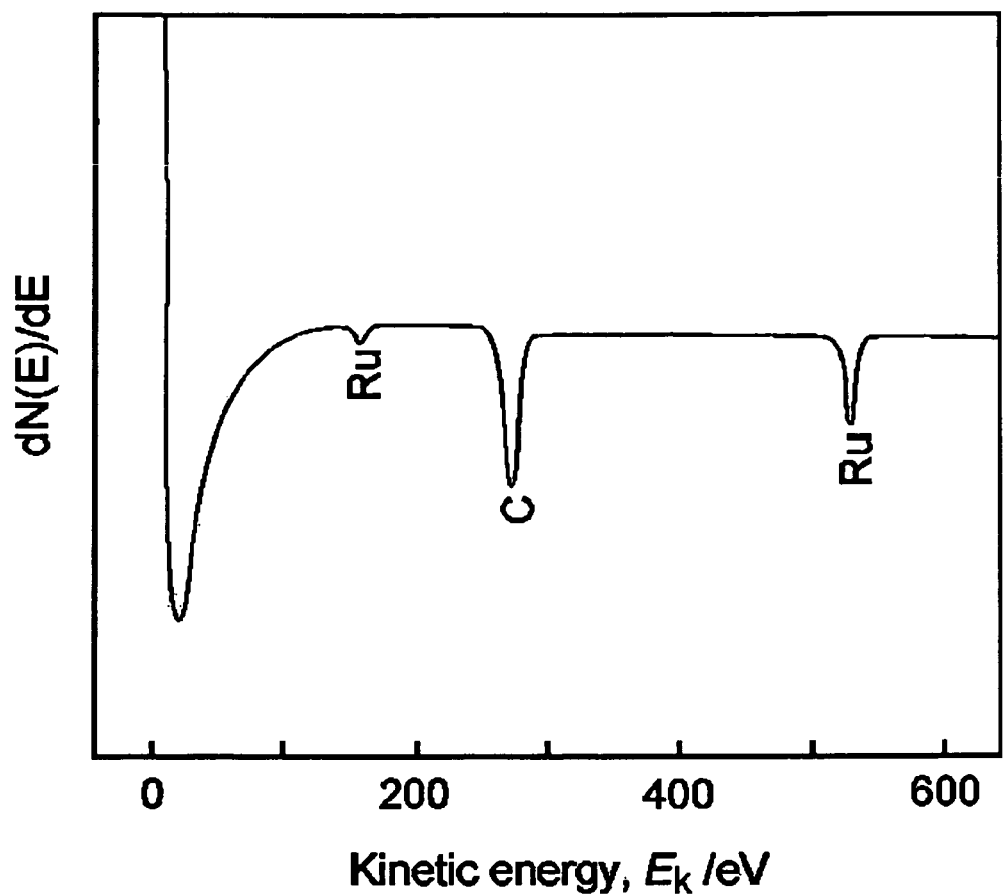
FIG. 10 is a drawing showing an AES spectrum of the film of Example 4.

In the particle-dispersed complex of Example 4, the composition was determined using Auger Electron Spectroscopy (AES) (manufactured by JEOL, JAMP-7100E). An AES spectrum of a film measured after etching was carried out for 300 seconds with argon ions is shown in FIG. 10. Carbon is present in the obtained film, and the carbon content calculated from the peak intensity ratio was 64 atom %, namely, the atomic number percent of carbon and ruthenium was (64:36).

Figure 11:
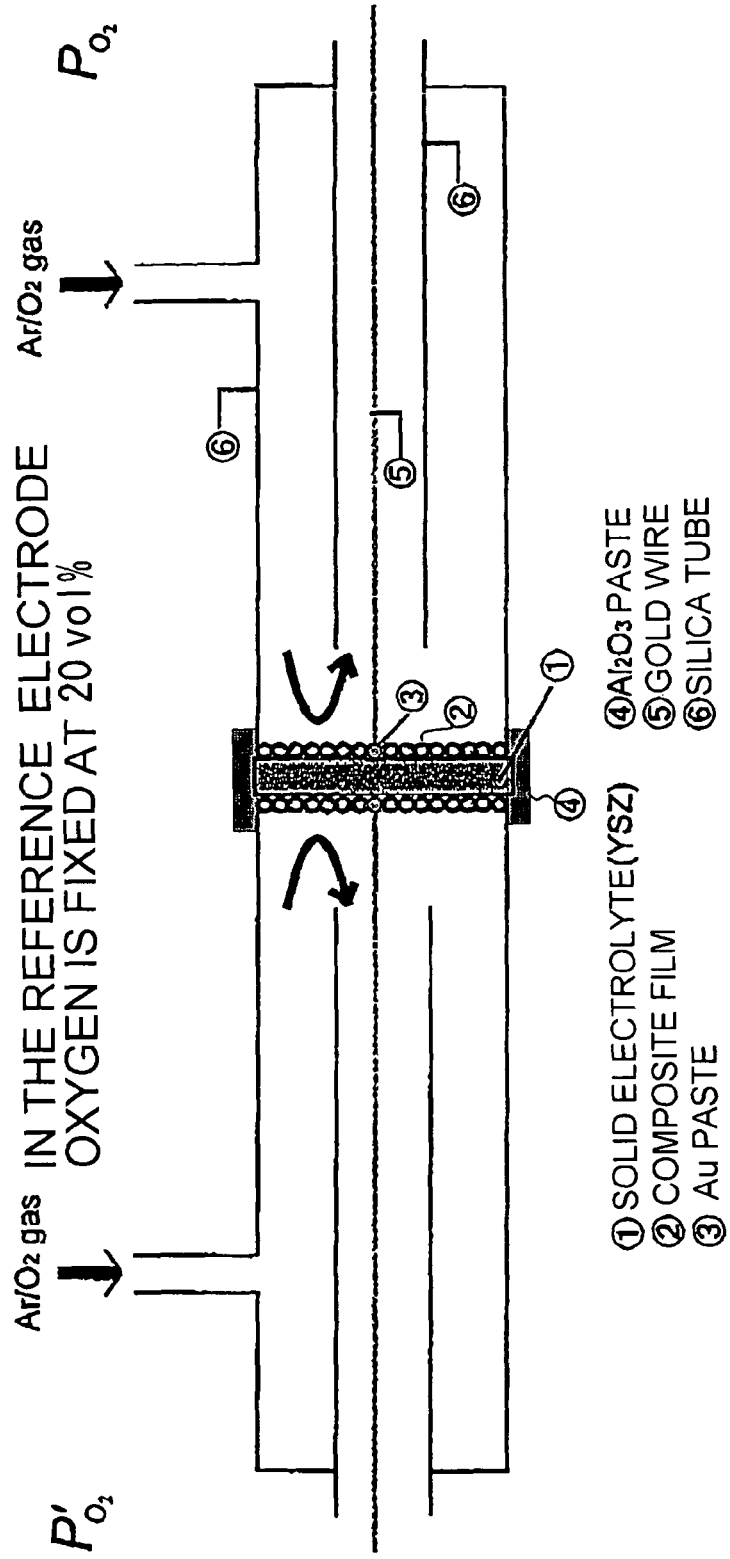
FIG. 11 is a model drawing of an oxygen gas concentration cell.
Figure 12:
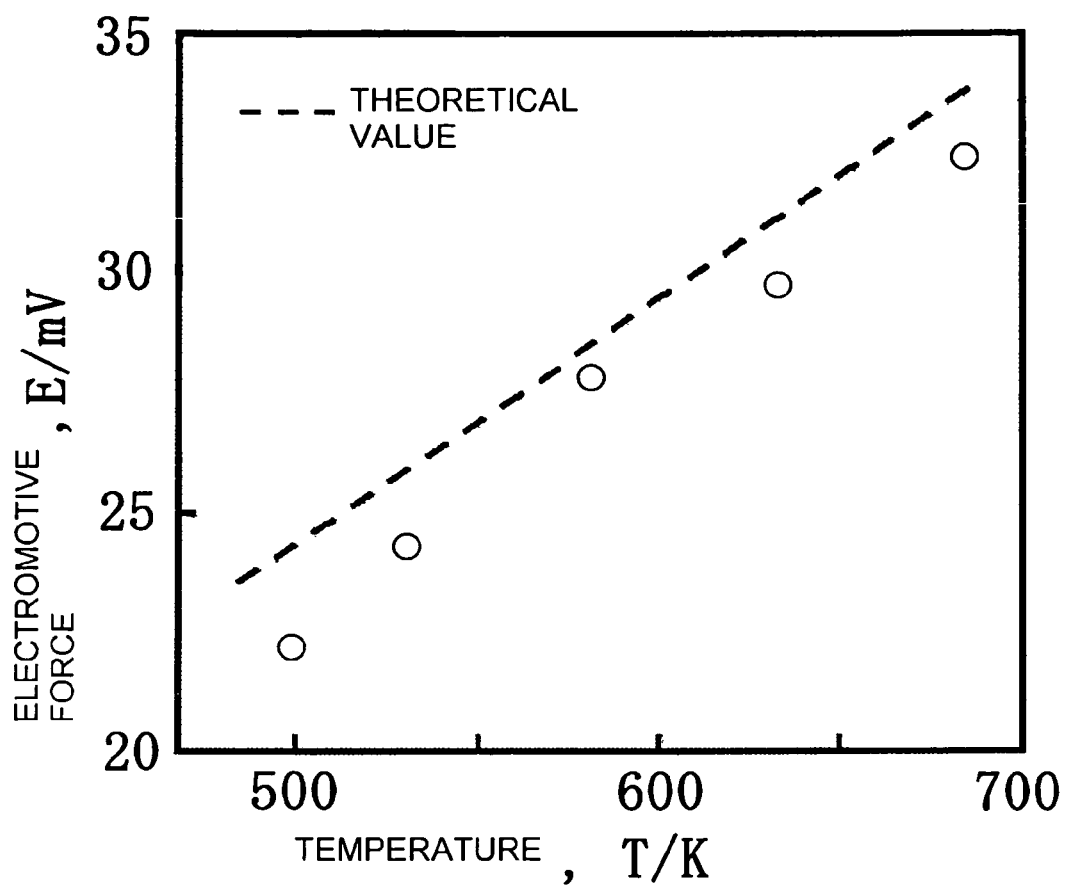
FIG. 12 is a graph showing the temperature dependency of the electromotive force of the oxygen gas concentration cell.
Figure 13:
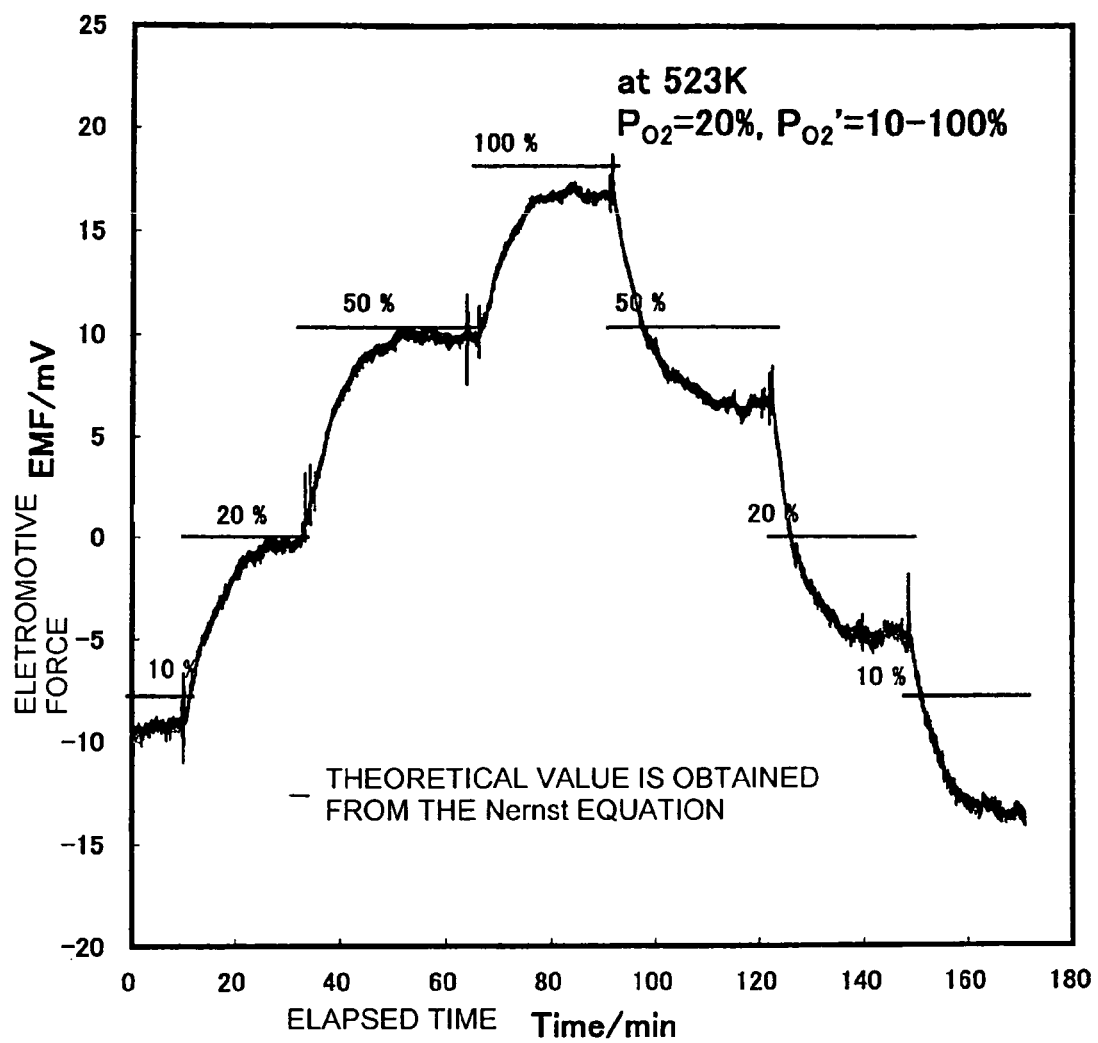
FIG. 13 is a graph showing changes of the electromotive force of the oxygen gas concentration cell as time advances when the oxygen concentration is changed at 250° C.
Figure 14:
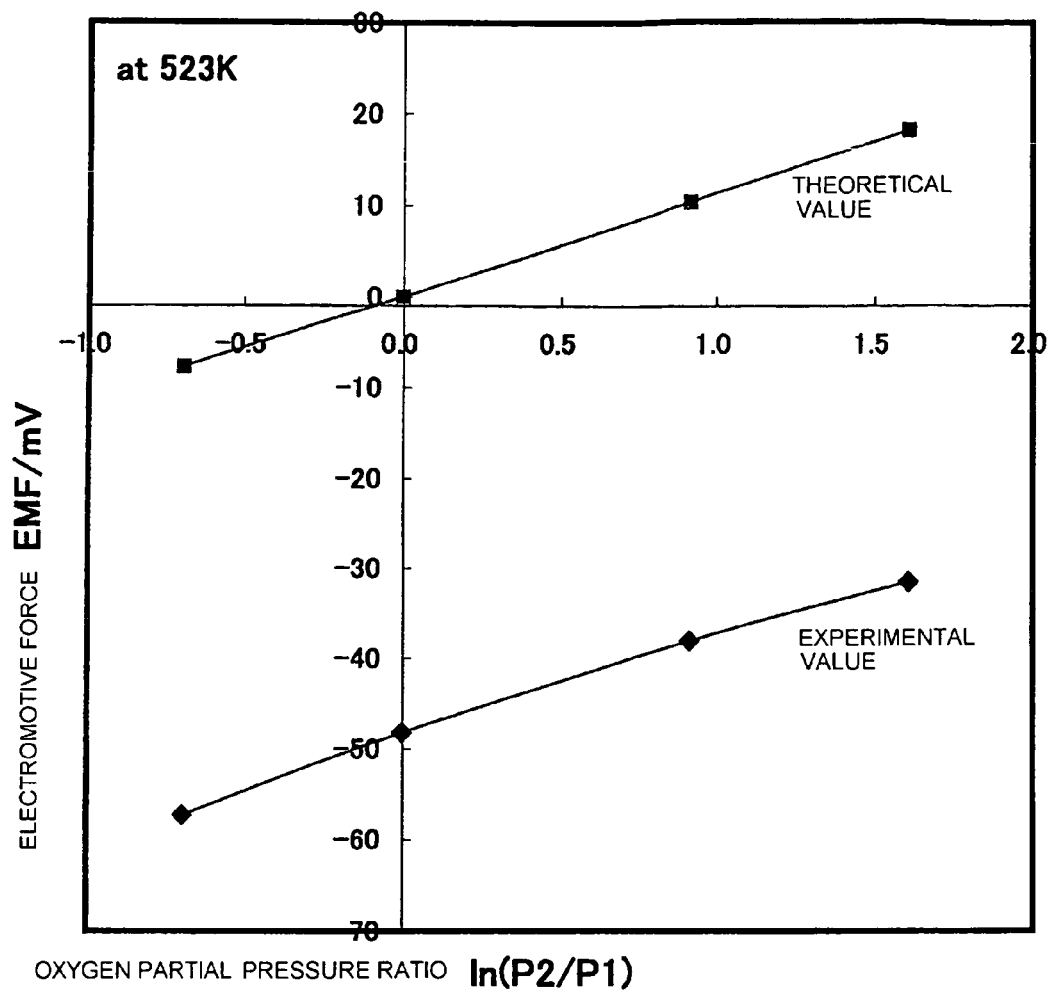
FIG. 14 is a graph showing the relationship between the oxygen partial pressure and the electromotive force at 250° C.

A solid electrolyte sensor was manufactured using a particle-dispersed complex that underwent film formation under the same conditions as the particle-dispersed complex of Example 4. A pattern diagram of an oxygen gas concentration cell is shown in FIG. 11. An oxygen gas concentration cell was manufactured by synthesizing a composite electrode on both sides of a YSZ solid electrolyte, and the electromotive force created between the electrodes was measured while the oxygen concentration of both sides was changed. FIG. 1 is a graph showing the temperature dependency of the electromotive force of the oxygen gas concentration cell. In a platinum electrode, an electromotive force was not displayed below 527° C., but the theoretical electromotive force calculated from the Nernst method even at 227° C. is shown for the case where a film of a particle-dispersed complex that underwent film formation under the same conditions as the particle-dispersed complex of Example 4 was made an electrode. FIG. 13 is a graph showing changes of the electromotive force of the oxygen gas concentration cell as time advances when the oxygen concentration was changed at a low temperature of 250° C. The oxygen concentration was raised in a stepwise manner in the range 10%~100%, and then when it was lowered in a stepwise manner, an electromotive force was obtained in accordance with the oxygen concentration, and that electromotive force was shown to match the theoretical value for the most part. Further, FIG. 14 is a graph showing the relationship between the oxygen partial pressure and the electromotive force at 250° C. When the experimental value was compared to the theoretical value, the electromotive force was measured as being low by a fixed proportion, and the electromotive force changed in accordance with the oxygen partial pressure. This profile is similar to the theoretical value and shows linear changes. From FIG. 12, FIG. 13 and FIG. 14, it was shown that the solid electrolyte sensor in which the particle-dispersed complex of Example 4 is made an electrode can detect oxygen concentration at a low temperature of 250° C., which has not occurred up to this point. Further, the response time of the electrode at 227° C. was 900 seconds.

Starting with Example 4, and then with the other examples, because ruthenium system fine particles are dispersed in a carbon matrix without aggregation, the ruthenium particles are highly active, and in the case where the electrode formed from the particle-dispersed complex of the examples is used as an electrode of an oxygen sensor or a solid electrolyte fuel cell, even the slightest of oxygen ion movement will be picked out as a signal, whereby operations at low temperature are possible. In this regard, by carrying out a remarkable reduction of the resistance of the interface of the electrode formed from the particle-dispersed complex of the examples and stabilized zirconia, high sensitivity to oxygen ion conduction is achieved. Further, it can be used as an electrode of an exhaust gas sensor of an automobile or the like which is a limiting current method sensor. Furthermore, it can be used as an electrode of an oxygen sensor in molten metal, in particular an oxygen sensor in molten metal which contains lead, bismuth.

The invention claimed is:

1. A particle-dispersed complex on a substrate, the particle dispersed complex comprising
a thin film matrix consisting of an aggregate of carbon black obtained by chemical vapor deposition (CVD); and
metallic ruthenium particles dispersed in and surrounded by the matrix, wherein
each of the particles has a particle diameter in a range of from 5 to 100 nm; and
every part of the entire surface of each of the particles makes contact with either the matrix or another of the particles.

2. The particle-dispersed complex according to claim 1, wherein an atomic number ratio of carbon to ruthenium in the particle-dispersed complex is in a range of from 30:70 to 70:30.

3. The particle-dispersed complex according to claim 1, wherein the matrix is deposited on a substrate by CVD at a substrate temperature of 350 to 450° C. with a source material comprising ruthenium dipivaloylmethanate and a carrier gas comprising greater than 9% and less than 23% of oxygen.

4. The particle-dispersed complex according to claim 1, wherein the complex is on an electrically conductive substrate.

5. The particle-dispersed complex according to claim 1, wherein the complex is on a solid electrolyte substrate.

6. The particle-dispersed complex according to claim 5, wherein an interfacial electrical conductivity a of the solid electrolyte substrate and a thin film formed from the particle-dispersed complex on a surface of the solid electrolyte substrate is in a range of from $10^{-6}$ $Sm^{-1}$ to $10^{-2}$ $Sm^{-1}$ at a temperature in a range of from 190 to 350° C.

7. The particle-dispersed complex according to claim 6, wherein the solid electrolyte substrate is a zirconium oxide substrate which includes a stabilizing agent.

8. The particle-dispersed complex according to claim 1, wherein the complex is a sensor electrode of a solid electrolyte sensor or an electrode for a solid electrolyte.

9. The particle-dispersed complex according to claim 1, wherein the complex is an electrochemical catalyst.

10. The particle-dispersed complex according to claim 8, wherein the complex is an electrochemical catalyst.

11. A solid electrolyte sensor, wherein the particle-dispersed complex according to claim 1 is formed as an electrode on a surface of a zirconium oxide substrate which includes a stabilizing agent.

12. A particle-dispersed complex on a solid electrically conductive substrate, the particle dispersed complex comprising
a thin film matrix consisting of an aggregate of carbon black obtained by chemical vapor deposition (CVD); and
metallic ruthenium particles dispersed in and surrounded by the matrix, wherein
each of the particles has a particle diameter in a range of from 5 to 100 nm; and every part of the entire surface of each of the particles makes contact with either the matrix or another of the particles,
wherein an interfacial electrical conductivity a of the solid electrically conductive substrate and a thin film formed from the particle-dispersed complex on a surface of the solid electrolyte substrate is in a range of from $10^{-6}$ $Sm^{-1}$ to $10^{-1}$ at a temperature in a range of from 190 to 350° C.

* * * * *